US00PP09761P

United States Patent [19]

Utecht

[11] Patent Number: Plant 9,761

[45] Date of Patent: Dec. 24, 1996

[54] GERANIUM PLANT NAMED 'FISALB'

[75] Inventor: Angelika Utecht, Montabaur, Germany

[73] Assignee: Florfis AG, Binningen, Switzerland

[21] Appl. No.: 518,892

[22] Filed: Aug. 29, 1995

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Foley & Lardner

[57] ABSTRACT

A new and distinct cultivar of geranium plant named Fisalb, characterized by its pure white flower color, open semi-double flower form, intense green foliage with good stability of chlorophyll, and compact plant habit with umbels borne well above the foliage.

1 Drawing Sheet

The present invention comprises a new and distinct cultivar of geranium, botanically known as *Pelargonium zonale,* and hereinafter referred to by the cultivar name Fisalb.

Fisalb is a product of a planned breeding program which had the objective of creating improved white flowering geranium cultivars with intense green foliage, good chlorophyll stability and at least slight zonation.

Fisalb was originated from a hybridization made by inventor Angelika Utecht in a controlled breeding program in Hillscheid, Germany, in 1990. The female parent was a white single flowered hybrid seedling with comparatively dark green foliage and compact plant habit. It was identified by the number K 87/1386/3 and was obtained by crossings between the commercial varieties Regina, a tetraploid line of Stadt Bern, and Perlenkette, disclosed in U.S. Plant Pat. No. 5,312. Regina is characterized by light salmon and white semi-double flowers, medium green foliage and tall plant habit. Stadt Bern has single orange-red flowers in combination with dark green zoned foliage, while Perlenkette is a very floriferous white flowering cultivar with light green foliage.

The male parent of Fisalb was an unnamed hybrid seedling identified as K 88/561/2 and characterized by semi-double white flowers and medium green foliage without zonation. It was derived from crosses between the commercial cutivars Dresdner Puppe Rosa, having single pink flowers with eyes, early flower response, medium green foliage with weak zonation; Stadt Bern, having orange-red single flowers and dark green, zoned foliage; Hoennefruehling, characterized by its single, light pink flowers, medium green foliage with strong zonation, and compact habit, and Bianca, characterized by single white flowers, late flower response, and light to medium green foliage without or with only very weak zonation.

Fisalb was discovered and selected as one flowering plant within the progeny of the stated cross by Angelika Utecht in 1991 in a controlled environment in Galdar, Gran Canaria, Spain. The first act of asexual reproduction of Fisalb was accomplished when vegetative cuttings were taken from the initial selection in June 1991 in a controlled environment in Galdar, Gran Canaria, Spain, by, or under the supervision of the inventor, Angelika Utecht.

Horticultural examination of plants grown from these cuttings initiated in May 1992 in Hillscheid, Federal Republic of Germany, and continuing thereafter, has demonstrated that the combination of characteristics as herein disclosed for Fisalb are firmly fixed and are retained through successive generation of asexual reproduction.

Fisalb has not been observed under all possible environmental conditions. The phenotype may vary significantly with variations in environment such as temperature, light intensity and daylength without, however, any variation in genotype.

The following observations, measurements, and comparisons describe plants grown in Hillscheid, Federal Republic of Germany under greenhouse conditions which approximate those generally used in commercial practice.

The following traits have been repeatedly observed and are determined to be basic characteristcs of Fisalb, which, in combination, distinguish this geranium as a new and distinct cultivar:

1. White flower color, without tendency to turn pink.
2. Semi-double flowers, slightly zygomorph in shape.
3. Intense green foliage with very weak zonation.
4. Compact plant habit.
5. Medium early flower response.

Of the many commercial cultivars known to the present inventor, the most similar in comparison to Fisalb are the patented cultivars Fisbal, disclosed in U.S. Plant Pat. No. 7,392, and Floscala, disclosed in a pending application.

Reference is made to attached chart A which compares certain characteristics of Fisalb to those same characteristics of Fisbal and Floscala. In general comparison to Fisbal, Fisalb has somewhat larger and differently shaped flowers (zygomorph vs. nearly round) and its white flower color has even less tendency to turn slightly pink. In contrast to Floscala, Fisalb has a more open flower form with fewer petals. The foliage color of Fisalb is intermediate, being more intense green than Fisbal, but not quite so dark green as Floscala.

The accompanying photographic drawing is a top perspective view showing typical flower and foliage of Fisalb, with colors being as true as possible with illustrations of this type.

In the following description, color references are made to The Royal Horticultural Society Colour Chart.

The color values were determined indoors from flowers taken from plants grown in a greenhouse in May 1994 in Hillscheid, Germany.

Classification:

*Botanical.*—A hybrid of the species *Pelargonium zonale* l'Hert.

*Commercial.*—Zonal geranium, cv., Fisalb.

Inflorescence

Umbel:

*Shape.*—Semi-spherical.

*Average diameter.*—95 mm.

*Average depth.*—65 mm.

*peduncle length.*—137 mm.
*Peduncle color.*—Medium green.
*Pedicel length.*—20 mm.
*Pedicel color.*—Medium green.
*Number of open flowers per umbel.*—20.

Corolla:
*Average diameter.*—44 mm.
*Form.*—Semi-double, zygomorph.
*Number of petals.*—5–7.
*Number of petaloids.*—0–1.
*Color (general tonality from a distance of three meters).*—White.
*Color of upper petals.*—155D.
*Color of lower petals.*—155D.
*Markings on upper petals.*—Tiny short pink lines at the base of upper petals.
*Color of lower surface of petals.*—155A–157A.
*Color of sepals.*—Light green.
*Number of sepals.*—5.

Bud:
*Shape.*—Elliptical.
*Color (adaxial).*—Green.
*Color (abaxial).*—Greenish white, about 150D.

Reproductive organs:
*Androecium.*—5–7 fertile anthers, white filaments, orange pollen.
*Gynoecium.*—5–6 lobed stigma.
*Seed.*—No seed set observed.

Spring flowering response period: In Hillscheid, Germany, in 1994 plants of Fisalb had on average 1.1 umbels with at least one flower opened 11 weeks after planting of unrooted cuttings.

Outdoor flower production: The flower count in 1994 in Hillscheid, Germany, indicated between 33 and 37 umbels per plant for May through August observation period.

Durability: Good shatter resistance, relatively good rain tolerance.

PLANT

Foliage:
*Form.*—Kidney-shaped.
*Margin.*—Bicrenated.
*Size of leaf.*—90 mm.
*Color of upper surface.*—Medium green, approximately 137 B–C.
*Color (zonation).*—Slightly darker green, not always visible.
*Tolerance of botrytis.*—Average.

General appearance and form:
*Internode length.*—0.5 cm.
*Branching pattern.*—1.9 cm branches per week.
*Height of plants.*—24 cm, (in June, based on 16-week-old plants).
*Ploidy.*—Tetraploid.

CHART A

| CHARACTERISTICS | FISALB | FISBAL | FLOSCALA |
|---|---|---|---|
| Flower form | zygomorph 5–7 petals | Nearly round 5–7 petals | Round 9–11 petals |
| Flower size | 44 mm | 40 mm | 39 mm |
| Pollen | Plenty, orange | Little, yellow orange | Little orange |
| Color of Leaf | Medium green 137 B–C | Medium green 137 C–D | Dark green 137 A |

It is claimed:

1. A new and distinct cultivar of geranium plant named Fisalb, as illustrated and described.

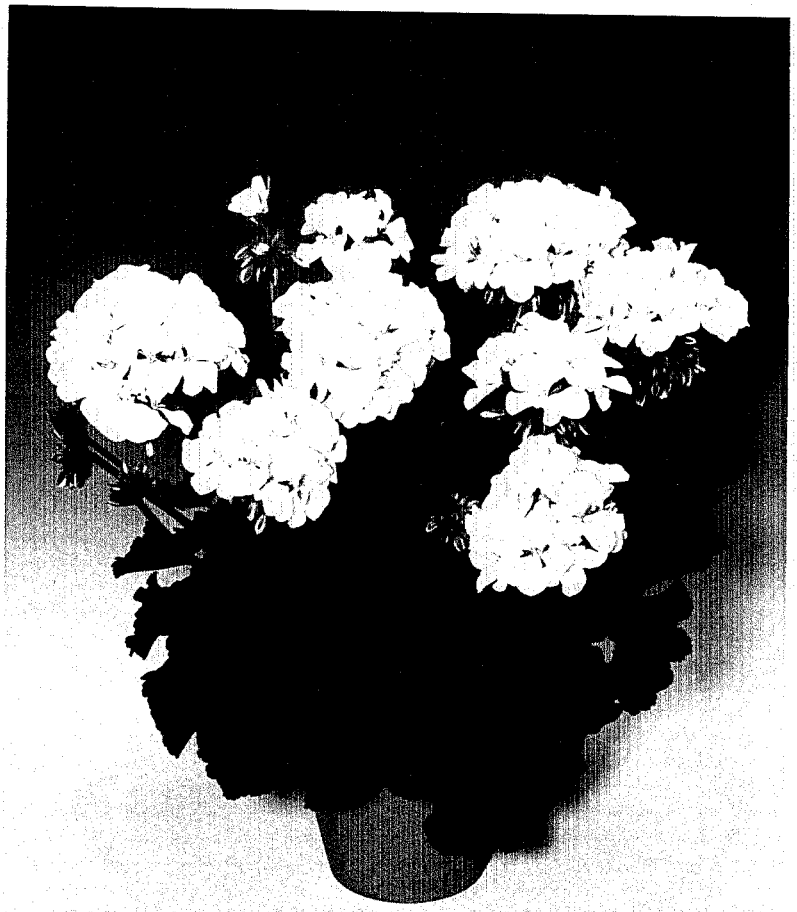

* * * * *